(12) United States Patent
Prema Mohanasundaram et al.

(10) Patent No.: US 11,819,209 B2
(45) Date of Patent: Nov. 21, 2023

(54) HAND-HELD SURGICAL INSTRUMENTS

(71) Applicant: Covidien LP, Mansfield, MA (US)

(72) Inventors: Suresh Kumar Prema Mohanasundaram, Chennai (IN); Brian J. Creston, Madison, CT (US); David M. Chowaniec, Rocky Hill, CT (US); Roanit A. Fernandes, Rocky Hill, CT (US); Hari Naga Mahesh Kalepu, Hyderabad (IN); Raja Kamaraj, Hyderabad (IN)

(73) Assignee: Covidien LP, Mansfield, MA (US)

( * ) Notice: Subject to any disclaimer, the term of this patent is extended or adjusted under 35 U.S.C. 154(b) by 200 days.

(21) Appl. No.: 17/392,783

(22) Filed: Aug. 3, 2021

(65) Prior Publication Data

US 2023/0038169 A1 Feb. 9, 2023

(51) Int. Cl.
*A61B 17/00* (2006.01)
*A61B 17/072* (2006.01)

(52) U.S. Cl.
CPC ............ *A61B 17/07207* (2013.01); *A61B 2017/0003* (2013.01); *A61B 2017/00119* (2013.01); *A61B 2017/00123* (2013.01); *A61B 2017/00367* (2013.01); *A61B 2017/00398* (2013.01); *A61B 2017/00477* (2013.01); *A61B 2017/00734* (2013.01)

(58) Field of Classification Search
CPC ...... A61B 17/07207; A61B 2017/0003; A61B 2017/00119; A61B 2017/00123; A61B 2017/00367; A61B 2017/00398; A61B 2017/00477; A61B 2017/00734; A61B 2017/00017; B25C 1/06; B25C 1/047

USPC .... 227/107, 140, 175.1–182.1; 173/200–212
See application file for complete search history.

(56) References Cited

U.S. PATENT DOCUMENTS

| | | |
|---|---|---|
| 2,777,340 A | 1/1957 | Hettwer et al. |
| 2,957,353 A | 10/1960 | Babacz |
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |

(Continued)

FOREIGN PATENT DOCUMENTS

| | | |
|---|---|---|
| AU | 2008229795 A1 | 4/2009 |
| CA | 2451558 A1 | 1/2003 |

(Continued)

OTHER PUBLICATIONS

International Search Report dated Oct. 24, 2022 and Written Opinion completed Oct. 14, 2022 corresponding to counterpart Int'l Patent Application PCT/IB2022/056888.

*Primary Examiner* — Robert F Long
(74) *Attorney, Agent, or Firm* — CARTER, DELUCA & FARRELL LLP

(57) ABSTRACT

A surgical instrument includes a motor-driven drive shaft, a distal firing rod coupled to a driven element of a surgical end effector, and a clutch mechanism coupled between the drive shaft and the distal firing rod. The clutch mechanism is configured to electrically connect the drive shaft and the distal firing rod upon the distal firing rod experiencing a threshold force. The electrical connection signals a processor that the threshold force has been exceeded.

18 Claims, 8 Drawing Sheets

(56) References Cited

U.S. PATENT DOCUMENTS

| | | | |
|---|---|---|---|
| 4,606,343 A | 8/1986 | Conta et al. | |
| 4,705,038 A | 11/1987 | Sjostrom et al. | |
| 4,722,685 A | 2/1988 | de Estrada et al. | |
| 4,823,807 A | 4/1989 | Russell et al. | |
| 4,869,719 A | 9/1989 | Hogan | |
| 4,874,181 A | 10/1989 | Hsu | |
| 5,129,118 A | 7/1992 | Walmesley | |
| 5,129,570 A | 7/1992 | Schulze et al. | |
| 5,152,744 A | 10/1992 | Krause et al. | |
| 5,299,848 A * | 4/1994 | Boyer | B23K 11/314 294/198 |
| 5,301,061 A | 4/1994 | Nakada et al. | |
| 5,312,023 A | 5/1994 | Green et al. | |
| 5,326,013 A | 7/1994 | Green et al. | |
| 5,350,355 A | 9/1994 | Sklar | |
| 5,383,874 A | 1/1995 | Jackson et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,400,267 A | 3/1995 | Denen et al. | |
| 5,411,508 A | 5/1995 | Bessler et al. | |
| 5,413,267 A | 5/1995 | Solyntjes et al. | |
| 5,427,087 A | 6/1995 | Ito et al. | |
| 5,467,911 A | 11/1995 | Tsuruta et al. | |
| 5,476,379 A | 12/1995 | Disel | |
| 5,487,499 A | 1/1996 | Sorrentino et al. | |
| 5,518,163 A | 5/1996 | Hooven | |
| 5,518,164 A | 5/1996 | Hooven | |
| 5,526,822 A | 6/1996 | Burbank et al. | |
| 5,529,235 A | 6/1996 | Boiarski et al. | |
| 5,535,934 A | 7/1996 | Boiarski et al. | |
| 5,535,937 A | 7/1996 | Boiarski et al. | |
| 5,540,375 A | 7/1996 | Bolanos et al. | |
| 5,540,706 A | 7/1996 | Aust et al. | |
| 5,542,594 A | 8/1996 | McKean et al. | |
| 5,549,637 A | 8/1996 | Crainich | |
| 5,553,675 A | 9/1996 | Pitzen et al. | |
| 5,562,239 A | 10/1996 | Boiarski et al. | |
| 5,564,615 A | 10/1996 | Bishop et al. | |
| 5,609,560 A | 3/1997 | Ichikawa et al. | |
| 5,628,446 A * | 5/1997 | Geiste | A61B 17/0684 227/176.1 |
| 5,632,432 A | 5/1997 | Schulze et al. | |
| 5,647,526 A | 7/1997 | Green et al. | |
| 5,653,374 A | 8/1997 | Young et al. | |
| 5,658,300 A | 8/1997 | Bito et al. | |
| 5,667,517 A | 9/1997 | Hooven | |
| 5,693,042 A | 12/1997 | Boiarski et al. | |
| 5,704,534 A | 1/1998 | Huitema et al. | |
| 5,713,505 A | 2/1998 | Huitema | |
| 5,762,603 A | 6/1998 | Thompson | |
| 5,779,130 A | 7/1998 | Alesi et al. | |
| 5,782,396 A | 7/1998 | Mastri et al. | |
| 5,782,397 A | 7/1998 | Koukline | |
| 5,797,536 A | 8/1998 | Smith et al. | |
| 5,820,009 A | 10/1998 | Melling et al. | |
| 5,863,159 A | 1/1999 | Lasko | |
| 5,908,427 A | 6/1999 | McKean et al. | |
| 5,954,259 A | 9/1999 | Viola et al. | |
| 5,964,774 A | 10/1999 | McKean et al. | |
| 5,968,012 A | 10/1999 | Ren et al. | |
| 5,993,454 A | 11/1999 | Longo | |
| 6,010,054 A | 1/2000 | Johnson et al. | |
| 6,017,354 A | 1/2000 | Culp et al. | |
| 6,032,849 A | 3/2000 | Mastri et al. | |
| 6,045,560 A | 4/2000 | McKean et al. | |
| 6,090,123 A | 7/2000 | Culp et al. | |
| 6,126,651 A | 10/2000 | Mayer | |
| 6,129,547 A | 10/2000 | Cise et al. | |
| 6,165,169 A | 12/2000 | Panescu et al. | |
| 6,197,002 B1 | 3/2001 | Peterson | |
| 6,221,023 B1 | 4/2001 | Matsuba et al. | |
| 6,239,732 B1 | 5/2001 | Cusey | |
| 6,241,139 B1 | 6/2001 | Milliman et al. | |
| 6,264,086 B1 | 7/2001 | McGuckin, Jr. | |
| 6,264,087 B1 | 7/2001 | Whitman | |
| 6,302,311 B1 | 10/2001 | Adams et al. | |
| 6,315,184 B1 | 11/2001 | Whitman | |
| 6,321,855 B1 | 11/2001 | Barnes | |
| 6,329,778 B1 | 12/2001 | Culp et al. | |
| 6,343,731 B1 | 2/2002 | Adams et al. | |
| 6,348,061 B1 | 2/2002 | Whitman | |
| 6,368,324 B1 | 4/2002 | Dinger et al. | |
| 6,371,909 B1 | 4/2002 | Hoeg et al. | |
| 6,434,507 B1 | 8/2002 | Clayton et al. | |
| 6,443,973 B1 | 9/2002 | Whitman | |
| 6,461,372 B1 | 10/2002 | Jensen et al. | |
| 6,488,197 B1 | 12/2002 | Whitman | |
| 6,491,201 B1 | 12/2002 | Whitman | |
| 6,533,157 B1 | 3/2003 | Whitman | |
| 6,537,280 B2 | 3/2003 | Dinger et al. | |
| 6,610,066 B2 | 8/2003 | Dinger et al. | |
| 6,611,793 B1 | 8/2003 | Burnside et al. | |
| 6,645,218 B1 | 11/2003 | Cassidy et al. | |
| 6,654,999 B2 | 12/2003 | Stoddard et al. | |
| 6,692,482 B2 | 2/2004 | Heller et al. | |
| 6,698,643 B2 | 3/2004 | Whitman | |
| 6,699,177 B1 | 3/2004 | Wang et al. | |
| 6,705,410 B2 * | 3/2004 | Ziegler | B25D 16/003 173/217 |
| 6,706,018 B2 | 3/2004 | Westlund et al. | |
| 6,716,233 B1 | 4/2004 | Whitman | |
| 6,743,240 B2 | 6/2004 | Smith et al. | |
| 6,783,533 B2 | 8/2004 | Green et al. | |
| 6,792,390 B1 | 9/2004 | Burnside et al. | |
| 6,793,652 B1 | 9/2004 | Whitman et al. | |
| 6,817,508 B1 | 11/2004 | Racenet et al. | |
| 6,830,174 B2 | 12/2004 | Hillstead et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 6,899,538 B2 | 5/2005 | Matoba | |
| 6,905,057 B2 | 6/2005 | Swayze et al. | |
| 6,959,852 B2 | 11/2005 | Shelton, IV et al. | |
| 6,964,363 B2 | 11/2005 | Wales et al. | |
| 6,981,628 B2 | 1/2006 | Wales | |
| 6,981,941 B2 | 1/2006 | Whitman et al. | |
| 6,986,451 B1 | 1/2006 | Mastri et al. | |
| 6,988,649 B2 | 1/2006 | Shelton, IV et al. | |
| 7,032,798 B2 | 4/2006 | Whitman et al. | |
| RE39,152 E | 6/2006 | Aust et al. | |
| 7,055,731 B2 | 6/2006 | Shelton, IV et al. | |
| 7,059,508 B2 | 6/2006 | Shelton, IV et al. | |
| 7,077,856 B2 | 7/2006 | Whitman | |
| 7,094,220 B2 | 8/2006 | Tanghoj et al. | |
| 7,111,769 B2 | 9/2006 | Wales et al. | |
| 7,122,029 B2 | 10/2006 | Koop et al. | |
| 7,140,528 B2 | 11/2006 | Shelton, IV | |
| 7,143,923 B2 | 12/2006 | Shelton, IV et al. | |
| 7,143,925 B2 | 12/2006 | Shelton, IV et al. | |
| 7,143,926 B2 | 12/2006 | Shelton, IV et al. | |
| 7,147,138 B2 | 12/2006 | Shelton, IV | |
| 7,172,104 B2 | 2/2007 | Scirica et al. | |
| 7,225,964 B2 | 6/2007 | Mastri et al. | |
| 7,238,021 B1 | 7/2007 | Johnson | |
| 7,246,734 B2 | 7/2007 | Shelton, IV | |
| 7,328,828 B2 | 2/2008 | Ortiz et al. | |
| 7,364,061 B2 | 4/2008 | Swayze et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,407,078 B2 | 8/2008 | Shelton, IV et al. | |
| 7,416,101 B2 | 8/2008 | Shelton, IV et al. | |
| 7,419,080 B2 | 9/2008 | Smith et al. | |
| 7,422,139 B2 | 9/2008 | Shelton, IV et al. | |
| 7,431,189 B2 | 10/2008 | Shelton, IV et al. | |
| 7,441,684 B2 | 10/2008 | Shelton, IV et al. | |
| 7,448,525 B2 | 11/2008 | Shelton, IV et al. | |
| 7,464,846 B2 | 12/2008 | Shelton, IV et al. | |
| 7,464,847 B2 | 12/2008 | Viola et al. | |
| 7,464,849 B2 | 12/2008 | Shelton, IV et al. | |
| 7,481,347 B2 | 1/2009 | Roy | |
| 7,481,824 B2 | 1/2009 | Boudreaux et al. | |
| 7,487,899 B2 | 2/2009 | Shelton, IV et al. | |

(56) References Cited

U.S. PATENT DOCUMENTS

| | | |
|---|---|---|
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,731,707 B2 | 6/2010 | Heller et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,798,999 B2 | 9/2010 | Bailey et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster et al. |
| 7,845,534 B2 | 12/2010 | Viola et al. |
| 7,845,537 B2 | 12/2010 | Shelton, IV et al. |
| 7,854,727 B2 | 12/2010 | Belsley |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,988,699 B2 | 8/2011 | Martz et al. |
| 7,992,758 B2 | 8/2011 | Whitman et al. |
| 8,016,178 B2 | 9/2011 | Olson et al. |
| 8,016,752 B2 | 9/2011 | Armstrong et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,025,621 B2 | 9/2011 | Ewaschuk et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,292,963 B2 | 10/2012 | Miller et al. |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,444,625 B2 | 5/2013 | Stalker et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,987,095 B2 | 6/2018 | Chowaniec et al. |
| 2001/0031975 A1 | 10/2001 | Whitman et al. |
| 2001/0034501 A1 | 10/2001 | Tom |
| 2002/0049454 A1 | 4/2002 | Whitman et al. |
| 2002/0128607 A1 | 9/2002 | Taury et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0193146 A1 | 9/2004 | Lee et al. |
| 2004/0260246 A1 | 12/2004 | Desmond |
| 2005/0004553 A1 | 1/2005 | Douk |
| 2005/0075711 A1 | 4/2005 | Neary |
| 2005/0096507 A1 | 5/2005 | Prosek |
| 2005/0131390 A1 | 6/2005 | Heinrich et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0200185 A1 | 9/2006 | Marchek et al. |
| 2006/0229573 A1 | 10/2006 | Lamborne |
| 2006/0259073 A1 | 11/2006 | Miyamoto et al. |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0151390 A1 | 7/2007 | Blumenkranz et al. |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |

(56) References Cited

U.S. PATENT DOCUMENTS

| | | |
|---|---|---|
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0164296 A1* | 7/2008 | Shelton ............ A61B 17/07207 227/175.1 |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0157092 A1 | 6/2009 | Blumenkranz et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2009/0314821 A1 | 12/2009 | Racenet |
| 2010/0069942 A1 | 3/2010 | Shelton, IV |
| 2010/0174327 A1 | 7/2010 | Radermacher |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2010/0228233 A1 | 9/2010 | Kahn |
| 2010/0294829 A1* | 11/2010 | Giordano ............... A61B 90/98 227/176.1 |
| 2010/0312257 A1 | 12/2010 | Aranyi |
| 2011/0017801 A1* | 1/2011 | Zemlok ............ A61B 17/07207 227/175.1 |
| 2011/0071508 A1 | 3/2011 | Duval et al. |
| 2011/0077673 A1 | 3/2011 | Grubac et al. |
| 2011/0118577 A1 | 5/2011 | Pfeiffer et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0184406 A1 | 7/2011 | Selkee |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0016402 A1 | 1/2012 | Weisshaupt et al. |
| 2012/0046577 A1 | 2/2012 | Soltz |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116248 A1 | 5/2012 | McWeeney et al. |
| 2012/0116368 A1 | 5/2012 | Viola |
| 2012/0123389 A1 | 5/2012 | Shafran |
| 2012/0143002 A1 | 6/2012 | Aranyi et al. |
| 2012/0150063 A1 | 6/2012 | Rea |
| 2012/0172924 A1 | 7/2012 | Allen, IV |
| 2012/0223121 A1 | 9/2012 | Viola et al. |
| 2012/0245426 A1 | 9/2012 | Salvas et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323081 A1 | 12/2012 | Son |
| 2012/0323226 A1 | 12/2012 | Chowaniec et al. |
| 2012/0330285 A1 | 12/2012 | Hartoumbekis et al. |
| 2013/0012983 A1 | 1/2013 | Kleyman |
| 2013/0018361 A1 | 1/2013 | Bryant |
| 2013/0053782 A1 | 2/2013 | Shelton, IV |
| 2013/0090531 A1 | 4/2013 | Ryan |
| 2013/0093149 A1 | 4/2013 | Saur et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0110085 A1 | 5/2013 | Adamson |
| 2013/0165942 A1 | 6/2013 | Tan-Malecki et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0220345 A1 | 8/2013 | Allphin et al. |
| 2013/0237950 A1 | 9/2013 | Gianotti et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0144970 A1 | 5/2014 | Aranyi et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0263561 A1 | 9/2014 | Castro et al. |
| 2014/0276932 A1 | 9/2014 | Williams et al. |
| 2014/0291378 A1* | 10/2014 | Shelton, IV ..... A61B 17/00234 227/175.2 |
| 2014/0373652 A1 | 12/2014 | Zergiebel et al. |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |
| 2017/0202605 A1* | 7/2017 | Shelton, IV ........ A61B 18/1447 |
| 2017/0311944 A1 | 11/2017 | Morgan et al. |
| 2018/0168610 A1 | 6/2018 | Shelton, IV et al. |
| 2019/0200977 A1 | 7/2019 | Shelton, IV et al. |
| 2021/0038222 A1 | 2/2021 | Park |
| 2021/0169477 A1* | 6/2021 | Shelton, IV ........ A61B 17/1155 |

FOREIGN PATENT DOCUMENTS

| | | | |
|---|---|---|---|
| CA | 2908109 A1 * | 11/2007 | ............ A61B 17/00 |
| CA | 2628336 A1 * | 10/2008 | |
| CN | 102247182 A | 11/2011 | |
| DE | 102008053842 A1 | 5/2010 | |
| DE | 102018103280 B4 * | 3/2022 | ............ B25B 27/146 |
| EP | 0634144 A1 | 1/1995 | |
| EP | 0648476 A1 | 4/1995 | |
| EP | 0686374 A2 | 12/1995 | |
| EP | 0705571 A1 | 4/1996 | |

(56) References Cited

FOREIGN PATENT DOCUMENTS

| | | | |
|---|---|---|---|
| EP | 1690502 | A1 | 8/2006 |
| EP | 1723913 | A1 | 11/2006 |
| EP | 1736112 | A1 | 12/2006 |
| EP | 1769754 | A1 | 4/2007 |
| EP | 1772105 | A1 | 4/2007 |
| EP | 1813199 | A1 | 8/2007 |
| EP | 1813203 | A2 | 8/2007 |
| EP | 1813211 | A2 | 8/2007 |
| EP | 1943954 | A2 | 7/2008 |
| EP | 1943956 | A2 | 7/2008 |
| EP | 1943958 | A1 | 7/2008 |
| EP | 1943976 | A2 | 7/2008 |
| EP | 1974676 | A1 | 10/2008 |
| EP | 2005898 | A2 | 12/2008 |
| EP | 2027819 | A1 | 2/2009 |
| EP | 2044890 | A1 | 4/2009 |
| EP | 2055243 | A2 | 5/2009 |
| EP | 2098170 | A2 | 9/2009 |
| EP | 2100561 | A2 | 9/2009 |
| EP | 2100562 | A2 | 9/2009 |
| EP | 2165664 | A2 | 3/2010 |
| EP | 2236098 | A2 | 10/2010 |
| EP | 2263568 | A2 | 12/2010 |
| EP | 2272443 | A1 | 1/2011 |
| EP | 2316345 | A1 | 5/2011 |
| EP | 2324776 | A2 | 5/2011 |
| EP | 2329773 | A1 | 6/2011 |
| EP | 2333509 | A1 | 6/2011 |
| EP | 2462878 | A1 | 6/2012 |
| EP | 2462880 | B1 | 6/2012 |
| EP | 2491872 | A1 | 8/2012 |
| EP | 2586382 | A2 | 5/2013 |
| EP | 2606834 | A2 | 6/2013 |
| EP | 2668910 | A2 | 12/2013 |
| EP | 2676615 | A2 | 12/2013 |
| EP | 2881046 | A2 | 6/2015 |
| ES | 2333509 | A1 | 2/2010 |
| JP | 08038488 | | 2/1996 |
| JP | 2005125075 | A | 5/2005 |
| JP | 2009106752 | A * | 5/2009 ....... A61B 17/00234 |
| KR | 20120022521 | A | 3/2012 |
| WO | 9915086 | A1 | 4/1999 |
| WO | 0072760 | A1 | 12/2000 |
| WO | 0072765 | A1 | 12/2000 |
| WO | 03000138 | A2 | 1/2003 |
| WO | 03026511 | A1 | 4/2003 |
| WO | 03030743 | A2 | 4/2003 |
| WO | 03065916 | A1 | 8/2003 |
| WO | 03077769 | A1 | 9/2003 |
| WO | 03090630 | A2 | 11/2003 |
| WO | 2004107989 | A1 | 12/2004 |
| WO | 2006042210 | A2 | 4/2006 |
| WO | 2007016290 | A2 | 2/2007 |
| WO | 2007026354 | A1 | 3/2007 |
| WO | 2007137304 | A2 | 11/2007 |
| WO | 2008131362 | A2 | 10/2008 |
| WO | 2008133956 | A2 | 11/2008 |
| WO | 2009039506 | A1 | 3/2009 |
| WO | 2007014355 | A3 | 4/2009 |
| WO | 2009132359 | A2 | 10/2009 |
| WO | 2009143092 | A1 | 11/2009 |
| WO | 2009149234 | A1 | 12/2009 |
| WO | 2010030114 | A2 | 3/2010 |
| WO | 2011108840 | A2 | 9/2011 |
| WO | 2012040984 | A1 | 4/2012 |

* cited by examiner

HAND-HELD SURGICAL INSTRUMENTS

BACKGROUND

A number of handle assembly manufacturers have developed product lines with proprietary drive systems for operating and/or manipulating electromechanical surgical instruments. In many instances, the electromechanical surgical instruments include a handle assembly, which is reusable, and disposable loading units and/or single use loading units, such as, for example, surgical end effectors that are selectively connected to the handle assembly prior to use and then disconnected from the handle assembly following use in order to be disposed of or in some instances sterilized for re-use.

SUMMARY

In one aspect of the present disclosure, a surgical instrument is provided and includes a handle assembly, an outer shaft, a distal firing rod, and a firing force clutch mechanism. The handle assembly includes a handle housing, a drive motor supported in the handle housing, and a drive shaft coupled to the drive motor and configured to translate in response to an activation of the drive motor. The outer shaft is coupled to the handle housing and the distal firing rod is slidably supported in the outer shaft. The distal firing rod has a distal end portion configured to operably couple to a driven member of a surgical end effector. The firing force clutch mechanism is coupled between a distal end portion of the drive shaft and a proximal end portion of the distal firing rod. The firing force clutch mechanism is configured to electrically connect the distal firing rod and the drive shaft to one another in response to a threshold axial force exerted on the firing force clutch mechanism.

In aspects, the surgical instrument may further include a processor disposed in the handle housing and in communication with the firing force clutch mechanism. The processor is configured disable the drive motor and/or issue an audible warning in response to the distal firing rod and the drive shaft electrically connecting to one another.

In aspects, the firing force clutch mechanism may include a spring configured to collapse in response to experiencing the threshold axial force such that the distal firing rod translates proximally and relative to the drive shaft.

In aspects, the firing force clutch mechanism may further include a proximal firing rod and a coupling bracket. The proximal firing rod may be fixed to the distal end portion of the drive shaft and in electrical communication with the drive shaft. The coupling bracket may be fixed to the distal firing rod and attached to the proximal firing rod. The spring may be disposed between the proximal firing rod and the coupling bracket to maintain the proximal firing rod out of electrical connection with the distal firing rod.

In aspects, the proximal firing rod may have a conductive element, and the distal firing rod may have a conductive element. The firing force clutch mechanism may be configured to transition, in response to the threshold axial force, from a first state to a second state. In the first state, the conductive elements are disconnected from one another. In the second state, the conductive elements are in electrical communication with one another.

In aspects, the surgical instrument may further include a battery supported in the handle housing and having a positive terminal and a negative terminal. The drive shaft may have a conductive element having a proximal end portion electrically connected to the positive terminal of the battery, and a distal end portion electrically connected to the conductive element of the proximal firing rod.

In aspects, the positive terminal of the battery may be fixed to the handle housing, and the proximal end portion of the conductive element of the drive shaft may be in sliding electrical contact with the positive terminal of the battery.

In aspects, the conductive element of the distal firing rod may be in electrical communication with the negative terminal of the battery such that when the firing force clutch mechanism transitions to the second state, a closed circuit loop is formed between the positive and negative terminals of the battery.

In aspects, the outer shaft may have a metal coupler fixed thereto and in sliding electrical contact with the conductive element of the distal firing rod. The metal coupler may be in electrical communication with the negative terminal of the battery via the outer shaft.

In aspects, the drive shaft may be a rack, and the handle assembly may further include an output gear rotatably driven by the drive motor and operably coupled to the rack such that rotation of the output gear results in the translation of the rack.

In accordance with further aspects of the disclosure, a hand-held surgical instrument is provided and includes a handle assembly an outer shaft, a distal firing rod, and a firing force clutch mechanism. The handle assembly includes a handle housing, a drive motor supported in the handle housing, a battery supported in the handle housing and having a positive terminal and a negative terminal, and a drive shaft coupled to the drive motor. The drive shaft is configured to translate in response to an activation of the drive motor and has a conductive element in electrical communication with the positive terminal of the battery. The outer shaft is coupled to the handle housing and extends distally relative to the handle housing. The distal firing rod is slidably supported in the outer shaft and has a distal end portion configured to operably couple to a driven member of a surgical end effector. The distal firing rod has a conductive element in electrical communication with the negative terminal of the battery. The firing force clutch mechanism is coupled between a distal end portion of the drive shaft and a proximal end portion of the distal firing rod such that the distal firing rod translates in response to the translation of the drive shaft. The firing force clutch mechanism is configured to electrically connect the conductive element of the distal firing rod and the conductive element of the drive shaft to one another in response to a threshold force exerted on the distal firing rod.

In aspects, the conductive element of the drive shaft may be an elongated metal strip in sliding electrical contact with the positive terminal of the battery, and the conductive element of the distal firing rod may be an elongated metal strip.

In aspects, the hand-held surgical instrument may further include a metal coupler fixed to the outer shaft. The metal strip of the distal firing rod may be in sliding contact with the metal coupler. The outer tube may be metallic or may have a metallic element in electrical communication with the negative terminal of the battery.

In aspects, the hand-held surgical instrument may further include a processor disposed in the handle housing and in communication with the battery. The processor may be configured to disable the drive motor and/or issue an audible warning in response to the conductive element of the distal firing rod and the conductive element of the drive shaft electrically connecting to one another.

In aspects, the firing force clutch mechanism may include a spring configured to collapse in response to the distal firing rod experiencing the threshold force such that the distal firing rod translates proximally and toward the drive shaft.

In aspects, the firing force clutch mechanism may further include a proximal firing rod and a coupling bracket coupling the distal firing rod and the proximal firing rod to one another. The proximal firing rod may be fixed to the distal end portion of the drive shaft and may be in electrical communication with the conductive element of the drive shaft. The spring may be configured to maintain the proximal firing rod out of electrical connection with the conductive element of the distal firing rod.

In aspects, the proximal firing rod may have a conductive element in electrical communication with the conductive element of the drive shaft. The firing force clutch mechanism may be configured to transition, in response to the threshold force, from a first state to a second state. In the first state, the conductive element of the proximal firing rod is electrically isolated from the conductive element of the distal firing rod. In the second state, the conductive element of the proximal firing rod is in electrical communication with the conductive element of the distal firing rod.

In aspects, the hand-held surgical instrument may further include the surgical end effector, which may be coupled to a distal end portion of the outer shaft.

In aspects, the firing force clutch mechanism may be configured to form a closed circuit loop between the positive and negative terminals of the battery upon electrically connecting the conductive element of the distal firing rod and the conductive element of the drive shaft to one another.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Aspects of the present disclosure are described herein with reference to the accompanying drawings, wherein.

DETAILED DESCRIPTION

Figure 1:
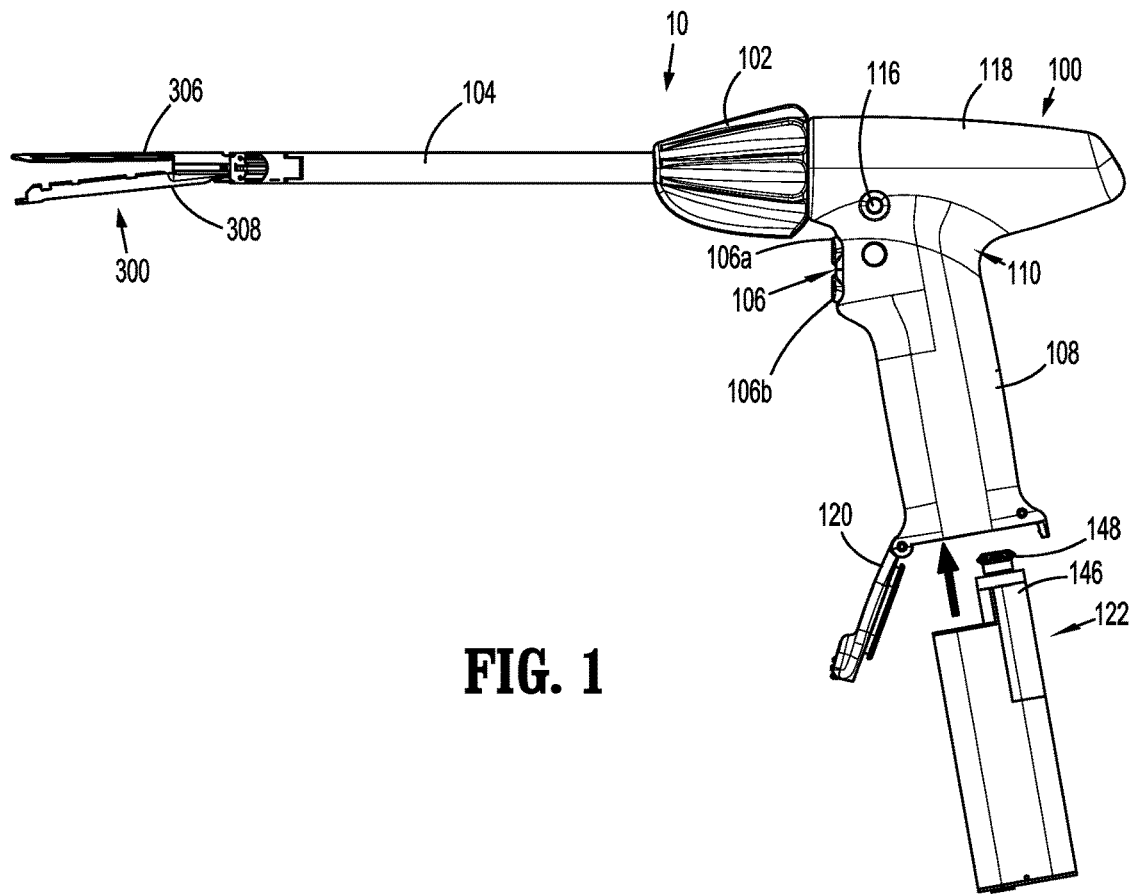
FIG. 1 is a side view illustrating a hand-held electromechanical surgical instrument including a handle assembly, with a power assembly shown separated, a shaft portion coupled to the handle assembly, and a surgical end effector coupled to the shaft portion.

Aspects of the presently disclosed surgical instrument are described in detail with reference to the drawings, in which like reference numerals designate identical or corresponding elements in each of the several views. As used herein the term "distal" refers to that portion of the surgical instrument, or component thereof, farther from the user, while the term "proximal" refers to that portion of the surgical instrument, or component thereof, closer to the user.

As will be described in detail below, provided is a surgical stapler including a mechanism that electromechanically disconnects a motor from a driven element upon receiving a threshold force that could potentially damage the surgical stapler if usage were to continue. The mechanism includes a spring that collapses under the threshold force thereby allowing for an electrical connection to form. Upon forming the electrical connection, a processor of the surgical stapler may be configured to cease operation of the motor and/or provide a warning to a user intended to discourage further activation of the motor. Other features and benefits of the disclosed surgical instruments are further detailed below.

Figure 2:
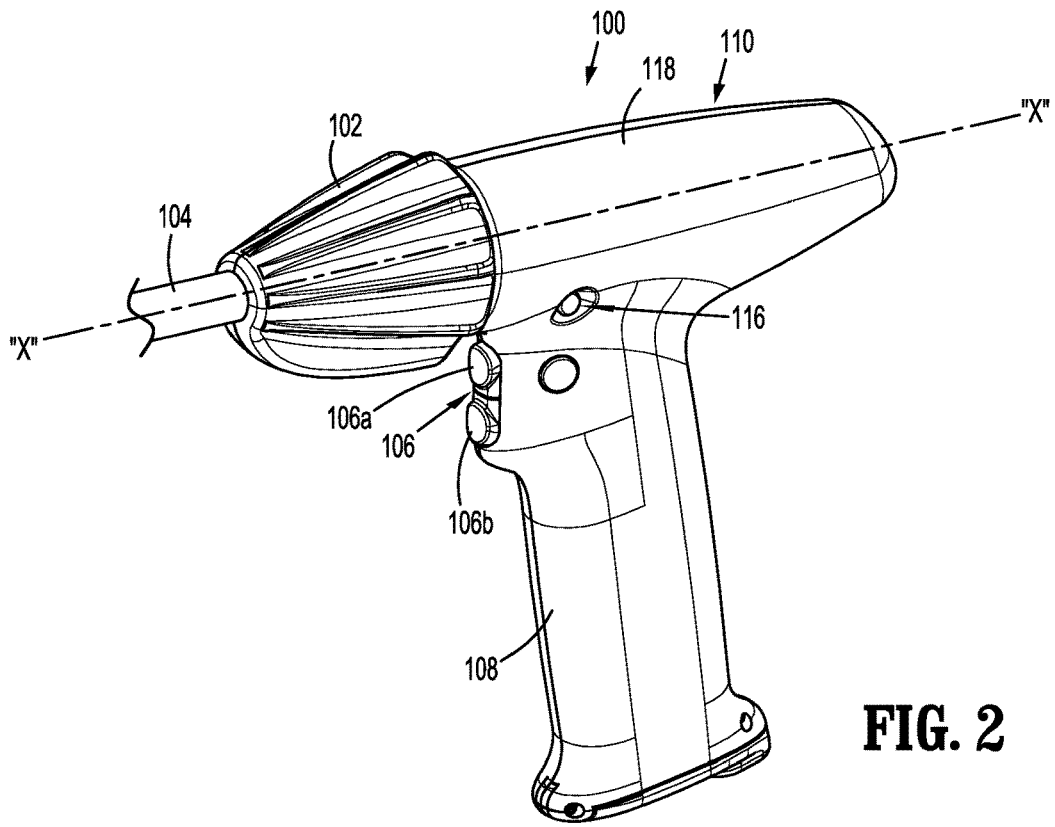
FIG. 2 is a partial perspective view illustrating the handle assembly of FIG. 1.

With reference to FIGS. 1 and 2, a surgical instrument, in accordance with an aspect of the present disclosure, is generally designated as 10, and is in the form of a powered hand-held electromechanical surgical instrument configured for selective coupling thereto of a plurality of different surgical end effectors, for example, the surgical end effector 300 of FIG. 1. The end effector 300 is configured for actuation and manipulation by the powered hand-held electromechanical surgical instrument 10. The hand-held electromechanical surgical instrument 10 includes a handle assembly 100, a knob housing 102 coupled to the handle assembly 100, and a shaft portion or outer shaft 104 extending distally from the knob housing 102 and configured for selective connection with a surgical attachment, such as, for example, the end effector 300. The knob housing 102 is rotatably coupled to the handle housing 110 and has the outer shaft 104 non-rotationally coupled thereto. As such, a manual rotation of the knob housing 102 results in a corresponding rotation of the end effector 300 (e.g., the end effector 300 rotates about a central longitudinal axis "X" defined by the outer shaft 104).

The handle assembly 100 includes a disposable and sterile handle housing 110 having a body, such as, for example, a barrel portion 118, a handle portion 108 extending perpendicularly downward from the barrel portion 118 or transversely and proximally from the barrel portion 118, and a hinged door 120 pivotably coupled to the handle portion 108. The door 120 is selectively opened and closed to allow for the insertion or removal of a non-sterile power assembly 122. The handle portion 108 and the door 120 each have an inner periphery collectively defining a sterile barrier 117 (FIG. 3) for the power assembly 122 upon closing the door 120. In aspects, a proximal end portion or any suitable location of the barrel portion 118 may have a clear window (not shown) to allow for viewing of a display (e.g., an LCD, not shown).

The handle assembly 100 has a fire switch 106 configured and adapted to actuate the various functions of the end effector 300. The fire switch 106 may be constructed as a toggle bar pivotably coupled to the handle portion 108 of the handle housing 110. An activation of the fire switch 106 activates a motor 112 (FIG. 3) to advance or retract a distal firing rod 180 (FIG. 4) in the outer shaft 104 depending on whether a top button 106a or a bottom button 106b of the fire switch 106 is actuated. The distal firing rod 180 (FIG. 4) is coupled to a drive assembly (not explicitly shown) of the end effector 300 (which includes a knife rod and an actuation sled), such that advancement of the distal firing rod 180 advances the drive assembly of the end effector 300, which closes jaw members 306, 308 of the end effector 300 and fires the end effector 300 when a safety switch 116 is in an actuated state.

Figure 3:
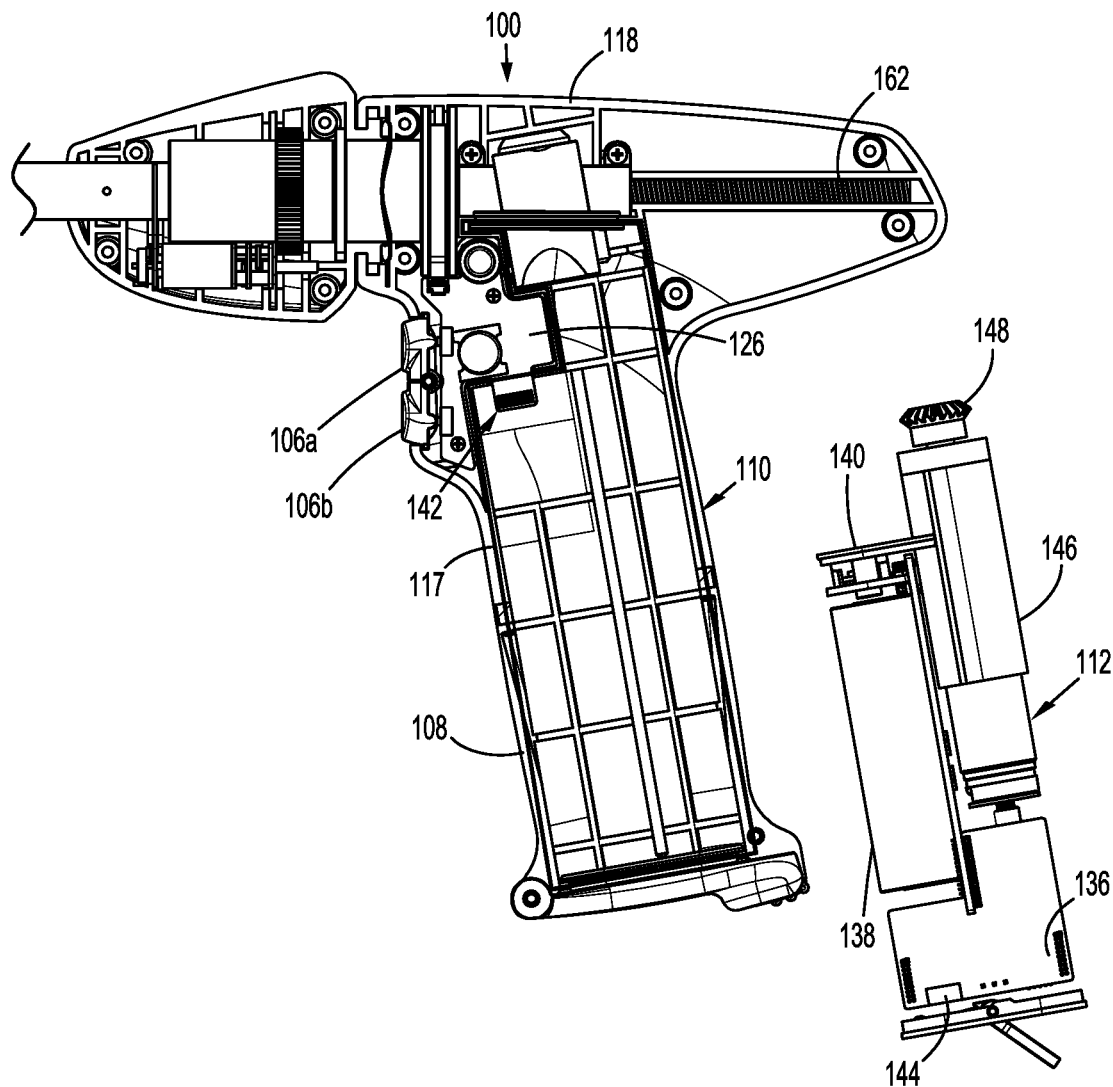
FIG. 3 is a side view, with a housing half of the handle housing removed, illustrating internal components of the handle assembly and the power assembly of FIG. 2 disassembled from the handle housing.

With reference to FIGS. 1 and 3, the reusable power assembly 122 of the handle assembly 100 includes the motor 112, such as, for example, an electrical drive motor, which is electrically connected or wirelessly connected to a motor controller or processor 136 and a battery 138. In aspects, the battery 138 has positive and negative terminals +, − (FIG. 10) and may include a boost circuit and may be rechargeable (e.g., wirelessly). The battery 138 has a card edge connector 140 configured for detachable receipt of a card edge header 142 of a printed circuit board 126 to allow for communication from the fire switch 106 to the battery 138. The processor 136 may include a USB charging connector 144 to allow for the battery 138 to be recharged with a USB charger or wirelessly (e.g., via induction).

The power assembly 122 further includes a gearbox 146, such as, for example, a planetary gearbox, operably coupled to the drive motor 112, and an output gear 148, such as, for example, a crown gear, drivingly coupled to the gearbox 146 and configured to rotate about a longitudinal axis defined by the gearbox 146. The planetary gearbox 146 multiplies torque while reducing speed. Rotation of the output gear 148 by the motor 112 functions to drive shafts and/or gear components of the handle assembly 100 to perform the various operations of the end effector 300. For example, the motor 112 is configured to move the jaw members 306, 308 of the end effector 300 relative to one another and to fire staples from the end effector 300.

Figure 4:
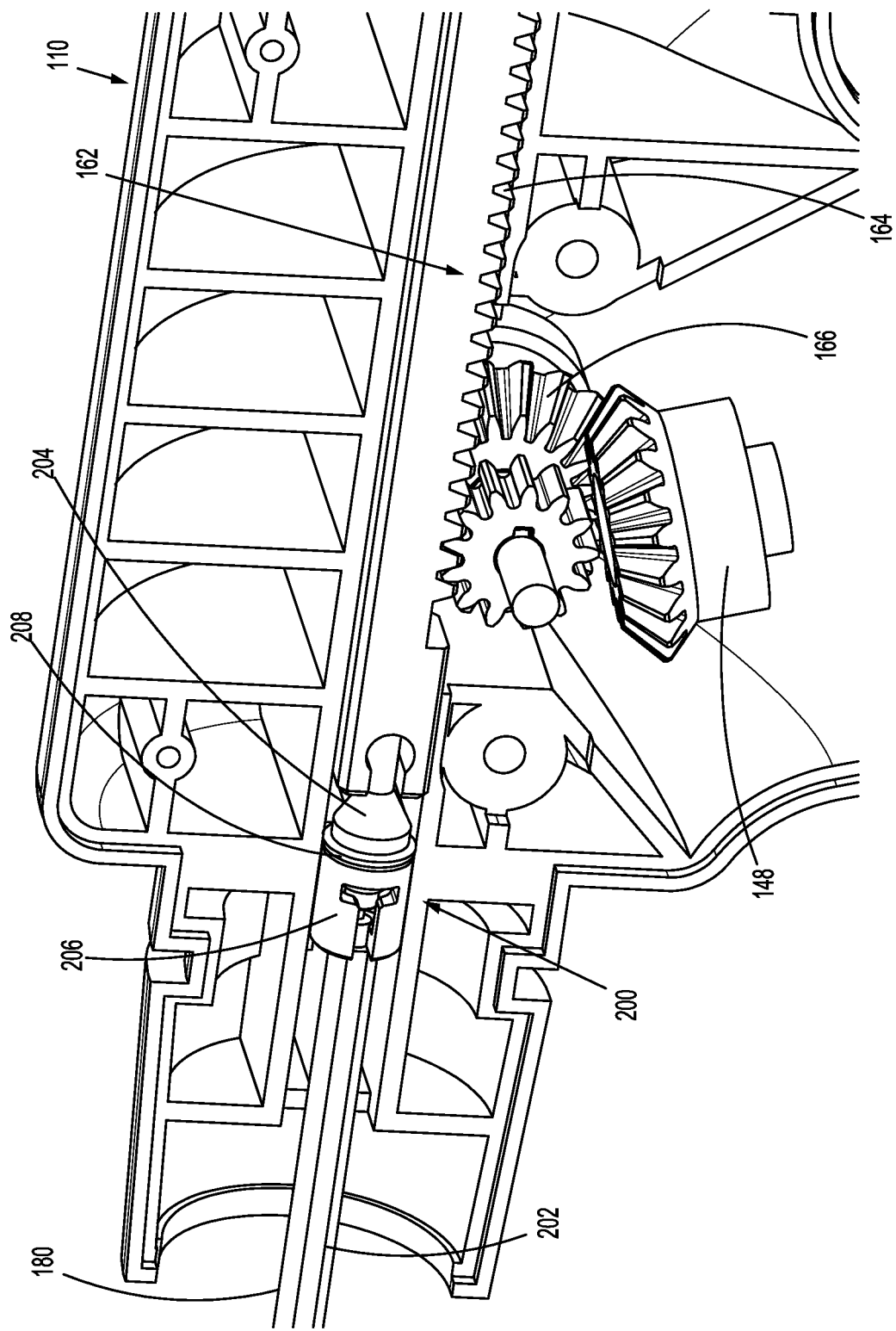
FIG. 4 is a side, perspective view, shown in cross-section, of the handle assembly and shaft assembly of FIG. 1 illustrating a firing force clutch mechanism.
Figure 5:
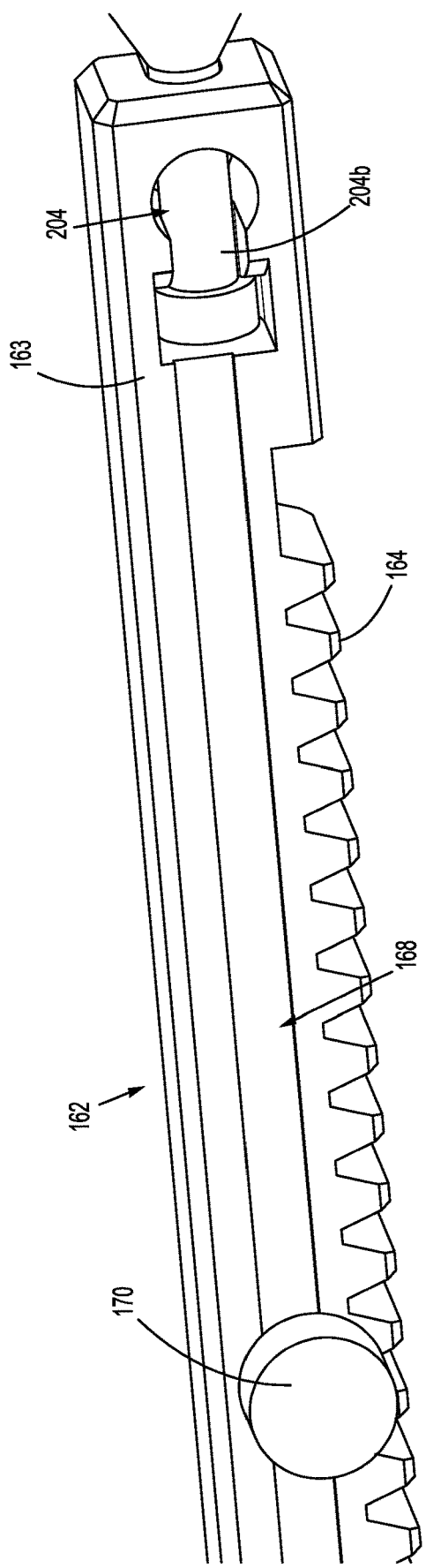
FIG. 5 is a side, perspective view illustrating a rack of the handle assembly.
Figure 6:
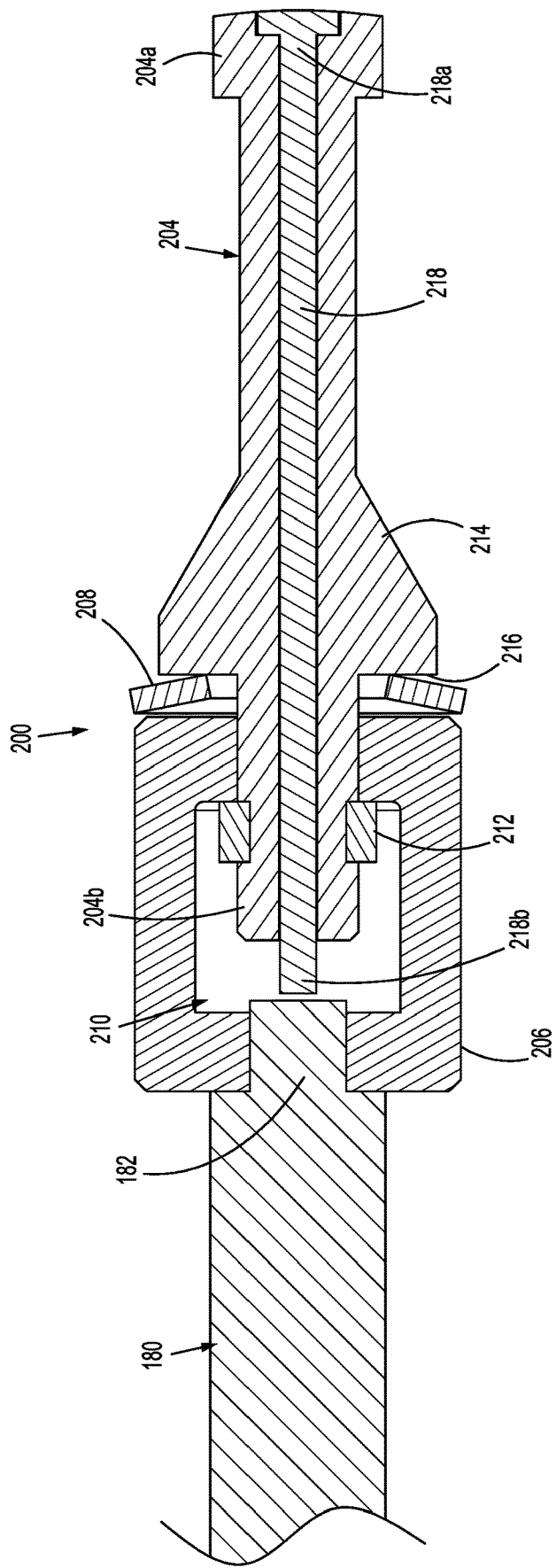
FIG. 6 is a longitudinal cross-sectional view illustrating components of the firing force clutch mechanism of FIG. 4.
Figure 7:
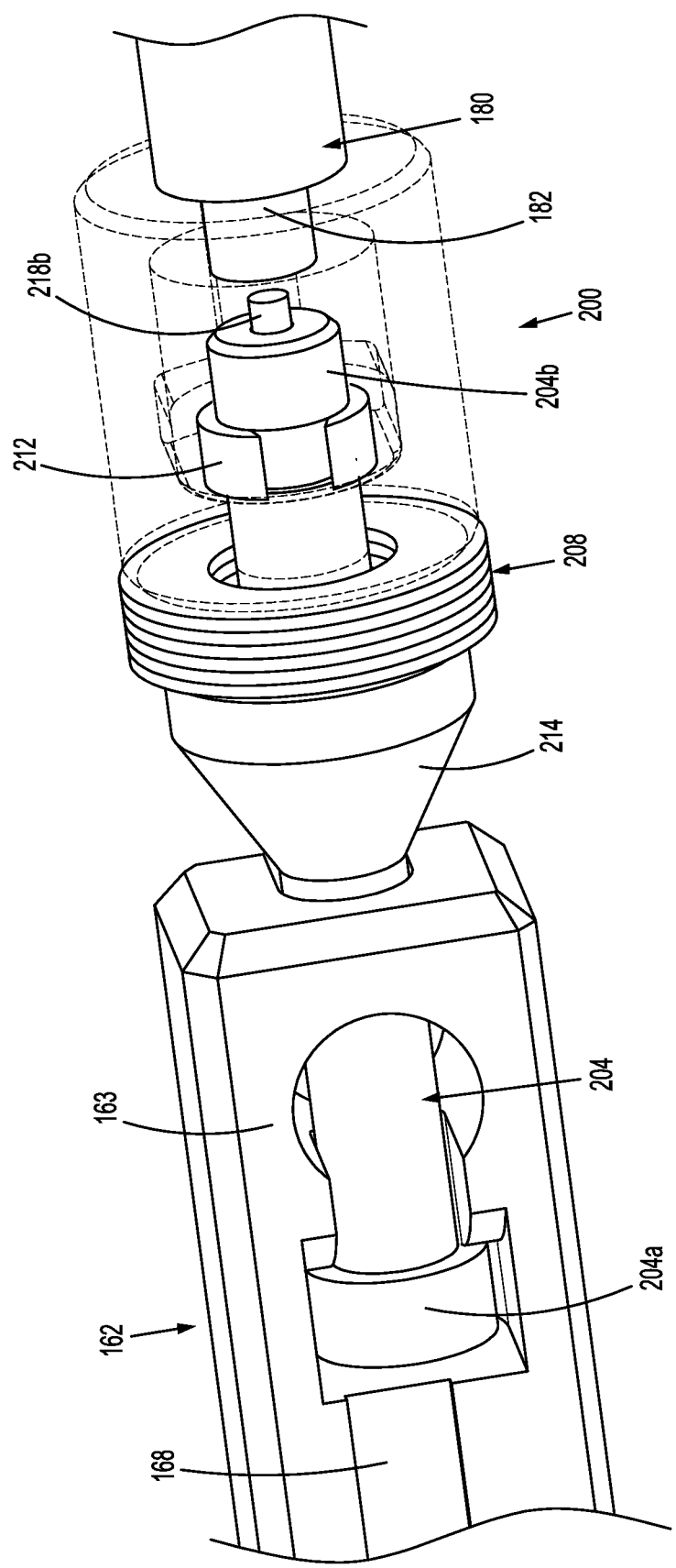
FIG. 7 is a side, perspective view illustrating the fire force clutch mechanism including the rack, a proximal firing rod, and a distal firing rod.

With reference to FIGS. 3-5, the handle assembly 100 includes a drive shaft, such as, for example, a rack 162 slidably supported in the barrel portion 118 of the handle housing 110 and extends parallel with the barrel portion 118. The rack 162 has a plurality of gear teeth 164 at its underside in meshing engagement with an idler gear 166, which operably couples the output gear 148 of the power assembly 122 to the rack 162. In aspects, the rack 162 may be directly engaged to the output gear 148. The rack 162 has an elongated conductive element, such as, for example, an elongated metal strip 168 (e.g., copper) extending along a lateral side of the rack 162. In aspects, the rack 162 may be fabricated from a conductive material (e.g., any suitable metal).

The metal strip 168 of the rack 162 is in electrical communication with the positive terminal + (FIG. 10) of the battery 138 via a metal coupler 170 (FIG. 5). The metal coupler 170 may be a metal disc fixed within the barrel portion 118 of the handle housing 110 and in electrical connection with the positive terminal + of the battery 138. The metal strip 168 of the rack 162 is in sliding electrical contact with the metal coupler 170 such that the electrical connection between the rack 162 and the positive terminal + of the battery 138 is maintained as the rack 162 is translated during use.

With reference to FIGS. 4-10, the surgical instrument 10 further includes a firing force clutch mechanism 200 interconnecting the rack 162 and the distal firing rod 180 such that a translation of the rack 162 results in a corresponding translation of the distal firing rod 180. The force firing clutch mechanism 200 is further configured to electrically isolate the metal strip 168 of the rack 162 from a corresponding metal strip 202 of the distal firing rod 180 until a threshold axial force is experienced by the distal firing rod 180, as will be described in further detail herein. The threshold axial force may be set to correspond to a force below that which is known to cause damage to any internal drive components of the surgical instrument 10 (e.g., the drive motor 112, the rack 162, or the distal firing rod 180). The threshold axial force may be caused by unsuitably thick tissue being clamped by the end effector 300, a hard object blocking travel of the knife blade or the staples of the end effector 300, etc.

With reference to FIGS. 4 and 6-9, the firing force clutch mechanism 200 includes a proximal firing rod or shaft 204, a coupling bracket 206, and a spacer or spring 208. The proximal firing rod 204 has a proximal end portion 204a fixed within a distal end portion 163 of the rack 162, and a distal end portion 204b received within a cavity 210 defined in the coupling bracket 206 such that the firing force clutch mechanism 200 translates with the rack 162. In aspects, the proximal firing rod 204 may be monolithically formed with the rack 162. The proximal firing rod 204 may have a retaining ring 212 fixed about the distal end portion 204b thereof. The retaining ring 212 is received within the cavity 210 of the coupling bracket 206 to prevent proximal movement of the proximal firing rod 204 relative to the coupling bracket 206. The proximal firing rod 204 may have a cone-shaped stop member 214 extending radially outward from an intermediate portion of the proximal firing rod 204. Other shapes for the stop member 214 are also contemplated. The stop member 214 of the proximal firing rod 204 has a distally-oriented planar face 216 in abutment with the spring 208.

The spring 208 of the firing force clutch mechanism 200 may be a cone disc (FIG. 6) or a plurality of stacked cone discs (FIGS. 7-8) disposed between the stop member 214 of the proximal firing rod 204 and a proximal end of the coupling bracket 206. The stiffness of the spring 208 is selected to correspond to the threshold force such that the spring 208 is configured to collapse or deform upon experiencing the threshold axial force. Other suitable components may be used instead of a cone disc, such as a crushable material, a coil spring, or the like.

The proximal firing rod 204 has a conductive element, such as, for example, an elongated metal (e.g., copper) core 218 (FIG. 6) extending therethrough. In other aspects, the proximal firing rod 204 may be fabricated from a conductive material. The metal core 218 has a proximal end portion 218a in permanent, direct electrical connection with the distal end portion of the metal strip 168 (FIG. 5) of the rack 162. A distal end portion 218b of the metal core 218 is received within the coupling bracket 206 and maintained, via the spring 208, in spaced relation from a proximal end portion 182 of the distal firing rod 180. A gap distance "D" (FIG. 8) defined between the distal end portion 204b of the proximal firing rod 204 and the proximal end portion 182 of the distal firing rod 180 is equal to or substantially equal to the axial distance the spring 208 is configured to collapse upon experiencing the threshold axial force.

Figure 8:
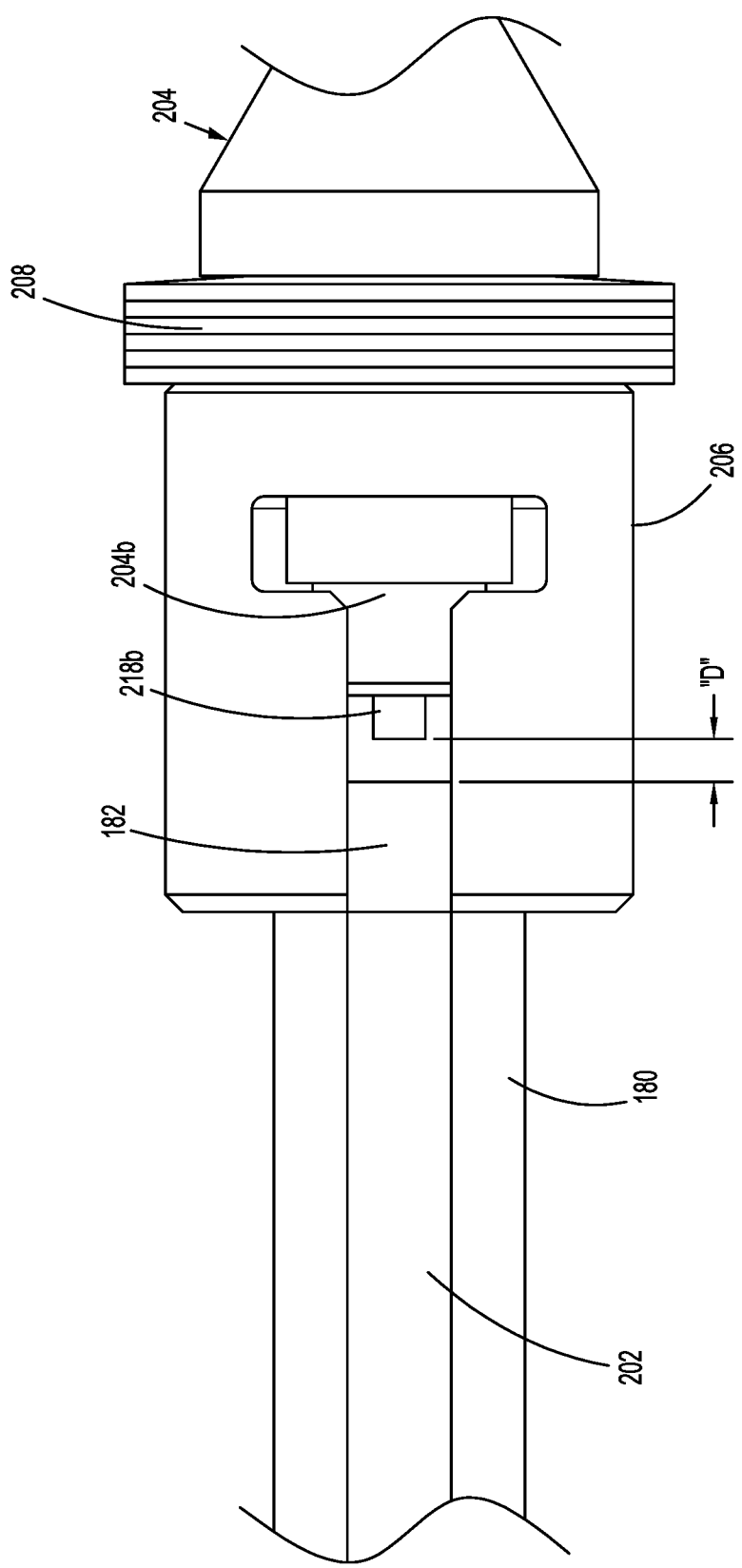
FIG. 8 is a side view illustrating a gap distance defined between two electrical contacts of the firing force clutch mechanism.
Figure 9:
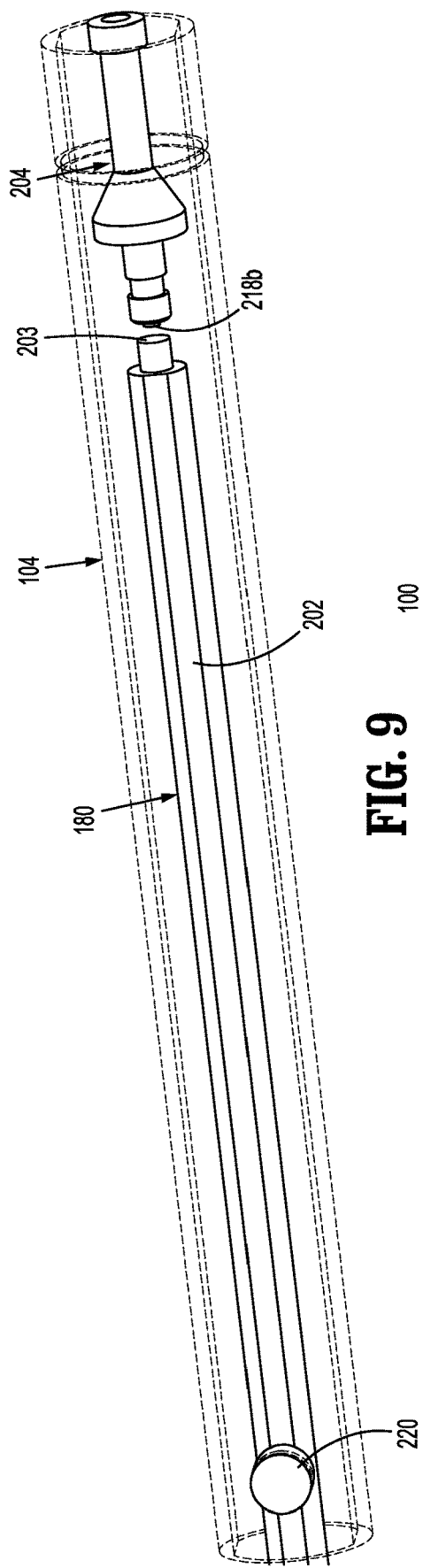
FIG. 9 is a side, perspective view illustrating the shaft assembly including components of the firing force clutch mechanism of FIG. 4.

With reference to FIGS. 8 and 9, the proximal end portion 182 of the distal firing rod 180 is fixed within the coupling bracket 208 (e.g., via welding) and is maintained in spaced relation from the distal end portion 204b of the proximal firing rod 204. In this way, during normal usage of the surgical instrument 10, the firing force clutch mechanism 200 allows for the distal firing rod 180 to translate with the proximal firing rod 204. The distal firing rod 180 extends through the outer shaft 104 (FIG. 1) and is slidably supported therein.

The distal firing rod 180 has an elongated conductive element, such as, for example, a metal (e.g., copper) strip 202 extending along its length. The metal strip 202 of the distal firing rod 180 has a proximal end portion 203 that faces the distal end portion 218b of the metal core 218 of the proximal firing rod 204. The proximal end portion 203 of the distal firing rod 180 and the distal end portion 218b of the metal core 218 of the proximal firing rod 204 are electrically isolated from one another due to the gap distance defined therebetween. In aspects, the proximal end portion 203 of the metal strip 202 of the distal firing rod 180 may be in the form of a metal core formed with the remainder of the metal strip 202.

Figure 10:
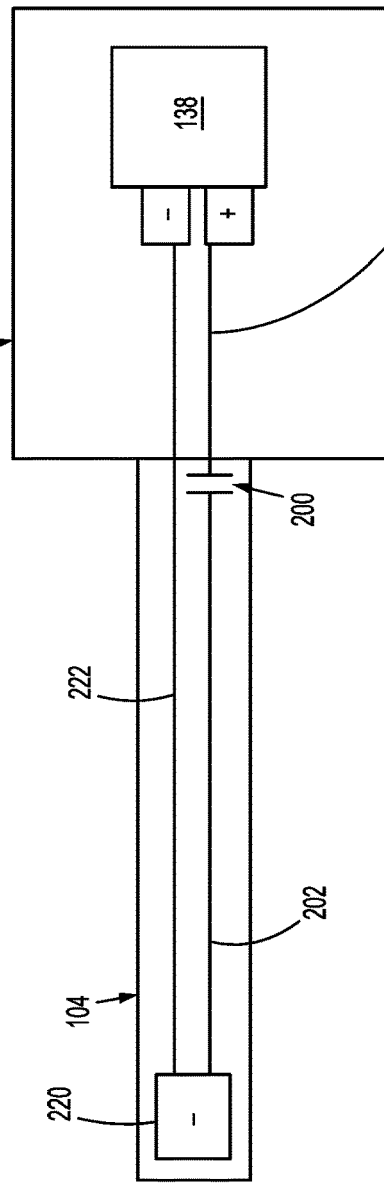
FIG. 10 is a schematic diagram of a circuit formed by the fire force clutch mechanism of the surgical instrument of FIG. 1.

With reference to FIGS. 8-10, the metal strip 202 of the distal firing rod 204 is in electrical communication with the negative terminal (−) of the battery 138 via a metal coupler 220. More specifically, the metal coupler 220 may be a metal disc fixed within the outer shaft 104 and in electrical connection with the negative terminal (−) of the battery 138. For example, the outer shaft 104 may be fabricated from a conductive material that allows for the transfer of electricity therethrough and to the negative terminal (−) of the battery 138. In other aspects, the outer shaft 104 may have a metal strip (not shown) that extends proximally from the metal coupler 220 and terminates proximally at the negative terminal (−) of the battery 138. It is contemplated that a wire or other suitable conductive traces 222 may be provided to electrically connect the negative terminal (−) of the battery 138 to the metal coupler 220.

The metal strip 202 of the distal firing rod 180 is in sliding electrical contact with the metal coupler 220 such that the electrical connection between the metal strip 202 of the distal firing rod 180 and the negative terminal (−) of the battery 138 is maintained as the distal firing rod 180 is translated during use. However, since the proximal and distal firing rods 204, 180 are electrically isolated from one another, the circuit (FIG. 10) defined between the negative and positive terminals (−), (+) of the battery 138 is maintained in an opened state whereby no electrical signal can be sent from the positive terminal (+) to the negative terminal − until the proximal and distal firing rods 204, 180 are approximated.

In operation, to effectuate an operational function of the surgical end effector 300 (FIG. 1), a clinician may actuate the fire button 106 of the handle assembly 100 to activate the drive motor 112, whereby the drive motor 112 rotates the output gear 148. The rack 162 translates distally in response to the rotation of the output gear 148. Since the distal firing rod 180 is coupled to the rack 162 via the firing force clutch mechanism 200, the distal firing rod 180 translates distally with the rack 162 to effectuate the operational function of the surgical end effector 300, such as closing of the surgical end effector 300 about tissue and to ultimately staple and cut tissue.

Under some circumstances, the surgical instrument 10 may experience an abnormal condition that provides an excess of resistance to actuation of the surgical end effector 300. For example, the thickness of the tissue may be too great for the end effector 300 to clamp, staple, and/or cut through, or there is a hard material impeding actuation. Under this abnormal condition, continued actuation of the drive motor 112 may result in an excessive firing reaction force that could damage the drive motor 112 and/or other internal components driven by the drive motor 112 (e.g., the output gear 148, the rack 162, the firing rods 180, 204, etc.). The firing force clutch mechanism 200 of the present disclosure prevents any damage from occurring, as will be described below.

Under the abnormal condition, the higher reaction force exerted by the distal firing rod 180 may eventually rise to the threshold axial force (set to a level below that which is known to result in damage to internal components) at which the spring 208 of the firing force clutch mechanism 200 is configured to collapse. As the spring 208 collapses between the proximal and distal firing rods 204, 180 under the threshold force, the proximal and distal firing rods 204, 180 slide relative and towards one another to overcome the gap distance "D" (FIG. 8) therebetween until the metal core 218 of the proximal firing rod 204 engages the metal strip 202 of the distal firing rod 180 to form an electrical connection therebetween.

With the proximal and distal firing rods 204, 180 forming an electrical connection therebetween, the circuit (FIG. 10) is closed, whereby the battery 138, in turn, sends an electrical signal from the positive terminal (+), through the metal strip 168 of the rack 162, the metal core 218 of the proximal firing rod 204, the metal strip 202 of the distal firing rod 180, and to the metal coupler 220 in the outer shaft 104. The electrical signal then passes from the metal coupler 220, through the outer shaft 104, and to the negative terminal (−) of the battery 138. The processor 136 receives the electrical signal, upon which the processor 136 may be configured to disable the drive motor 112 to prevent further actuation of the drive motor 112. In aspects, the processor 136 may be configured to send an audible or visual warning to the clinician that further actuation of the surgical instrument 10 is not recommended. In aspects, the battery 138 for actuating the drive motor 112 may be the same battery for sending the electrical signal, and in other aspects, there may be two distinct batteries.

Any of the components described herein may be fabricated from either metals, plastics, resins, composites or the like taking into consideration strength, durability, wearability, weight, resistance to corrosion, ease of manufacturing, cost of manufacturing, and the like. Any of the gears disclosed herein may be configured as any suitable gear, such as bevel gears, spur gears, spiral gears, worm gears, or the like.

It will be understood that various modifications may be made to the aspects of the presently disclosed surgical instruments including switch assemblies. Therefore, the above description should not be construed as limiting, but merely as exemplifications of aspects. Those skilled in the art will envision other modifications within the scope and spirit of the present disclosure.

We claim:
1. A surgical instrument, comprising:
a handle assembly including:
a handle housing;
a drive motor supported in the handle housing; and
a drive shaft coupled to the drive motor and configured to translate in response to an activation of the drive motor;
an outer shaft coupled to the handle housing;

a distal firing rod slidably supported in the outer shaft and having a distal end portion configured to operably couple to a driven member of a surgical end effector; and a firing force clutch mechanism coupled between a distal end portion of the drive shaft and a proximal end portion of the distal firing rod, wherein the firing force clutch mechanism is configured to electrically connect the distal firing rod and the drive shaft to one another in response to a threshold axial force exerted on the firing force clutch mechanism, wherein the firing force clutch mechanism includes:

a spring configured to collapse in response to experiencing the threshold axial force such that the distal firing rod translates proximally and relative to the drive shaft;

a proximal firing rod fixed to the distal end portion of the drive shaft and being in electrical communication with the drive shaft; and a coupling bracket fixed to the distal firing rod and attached to the proximal firing rod, the spring being disposed between the proximal firing rod and the coupling bracket to maintain the proximal firing rod out of electrical connection with the distal firing rod.

2. The surgical instrument according to claim 1, further comprising a processor disposed in the handle housing and in communication with the firing force clutch mechanism, wherein the processor is configured to at least one of disable the drive motor or issue an audible warning in response to the distal firing rod and the drive shaft electrically connecting to one another.

3. The surgical instrument according to claim 1, wherein the proximal firing rod has a conductive element, and the distal firing rod has a conductive element, the firing force clutch mechanism being configured to transition, in response to the threshold axial force, from a first state, in which the conductive elements are disconnected from one another, to a second state, in which the conductive elements are in electrical communication with one another.

4. The surgical instrument according to claim 3, further comprising a battery supported in the handle housing and having a positive terminal and a negative terminal, wherein the drive shaft has a conductive element having a proximal end portion electrically connected to the positive terminal of the battery and a distal end portion electrically connected to the conductive element of the proximal firing rod.

5. The surgical instrument according to claim 4, wherein the positive terminal of the battery is fixed to the handle housing, and the proximal end portion of the conductive element of the drive shaft is in sliding electrical contact with the positive terminal of the battery.

6. The surgical instrument according to claim 5, wherein the conductive element of the distal firing rod is in electrical communication with the negative terminal of the battery such that when the firing force clutch mechanism transitions to the second state, a closed circuit loop is formed between the positive and negative terminals of the battery.

7. The surgical instrument according to claim 6, wherein the outer shaft has a metal coupler fixed thereto and in sliding electrical contact with the conductive element of the distal firing rod, the metal coupler in electrical communication with the negative terminal of the battery via the outer shaft.

8. The surgical instrument according to claim 1, wherein the drive shaft is a rack, and the handle assembly further includes an output gear rotatably driven by the drive motor and operably coupled to the rack such that rotation of the output gear results in the translation of the rack.

9. A hand-held surgical instrument, comprising:
a handle assembly including:
a handle housing;
a drive motor supported in the handle housing;
a battery supported in the handle housing and having a positive terminal and a negative terminal; and
a drive shaft coupled to the drive motor and configured to translate in response to an activation of the drive motor, the drive shaft having a conductive element in electrical communication with the positive terminal of the battery;

an outer shaft coupled to the handle housing and extending distally relative to the handle housing;

a distal firing rod slidably supported in the outer shaft and having a distal end portion configured to operably couple to a driven member of a surgical end effector, the distal firing rod having a conductive element in electrical communication with the negative terminal of the battery; and a firing force clutch mechanism coupled between a distal end portion of the drive shaft and a proximal end portion of the distal firing rod such that the distal firing rod translates in response to the translation of the drive shaft, wherein the firing force clutch mechanism is configured to electrically connect the conductive element of the distal firing rod and the conductive element of the drive shaft to one another in response to a threshold force exerted on the distal firing rod.

10. The hand-held surgical instrument according to claim 9, wherein the conductive element of the drive shaft is an elongated metal strip in sliding electrical contact with the positive terminal of the battery, and the conductive element of the distal firing rod is an elongated metal strip.

11. The hand-held surgical instrument according to claim 10, further comprising a metal coupler fixed to the outer shaft, the metal strip of the distal firing rod being in sliding contact with the metal coupler, wherein the outer tube is metallic or has a metallic element in electrical communication with the negative terminal of the battery.

12. The hand-held surgical instrument according to claim 9, further comprising a processor disposed in the handle housing and in communication with the battery, wherein the processor is configured to at least one of disable the drive motor or issue an audible warning in response to the conductive element of the distal firing rod and the conductive element of the drive shaft electrically connecting to one another.

13. The hand-held surgical instrument according to claim 9, wherein the firing force clutch mechanism includes a spring configured to collapse in response to the distal firing rod experiencing the threshold force such that the distal firing rod translates proximally and toward the drive shaft.

14. The hand-held surgical instrument according to claim 13, wherein the firing force clutch mechanism further includes:
a proximal firing rod fixed to the distal end portion of the drive shaft and being in electrical communication with the conductive element of the drive shaft; and
a coupling bracket coupling the distal firing rod and the proximal firing rod to one another, the spring being configured to maintain the proximal firing rod out of electrical connection with the conductive element of the distal firing rod.

15. The hand-held surgical instrument according to claim 14, wherein the proximal firing rod has a conductive element in electrical communication with the conductive element of the drive shaft, the firing force clutch mechanism being configured to transition, in response to the threshold force, from a first state, in which the conductive element of the proximal firing rod is electrically isolated from the conductive element of the distal firing rod, to a second state, in which the conductive element of the proximal firing rod is in electrical communication with the conductive element of the distal firing rod.

16. The hand-held surgical instrument according to claim 9, wherein the drive shaft is a rack, and the handle assembly further includes an output gear rotatably driven by the drive motor and operably coupled to the rack such that rotation of the output gear results in the translation of the rack.

17. The hand-held surgical instrument according to claim 9, further comprising the surgical end effector, wherein the surgical end effector is coupled to a distal end portion of the outer shaft.

18. The hand-held surgical instrument according to claim 9, wherein the firing force clutch mechanism is configured to form a closed circuit loop between the positive and negative terminals of the battery upon electrically connecting the conductive element of the distal firing rod and the conductive element of the drive shaft to one another.

* * * * *